(12) United States Patent
Rantala

(10) Patent No.: US 8,456,295 B2
(45) Date of Patent: Jun. 4, 2013

(54) ALARM GENERATION METHOD FOR PATIENT MONITORING, PHYSIOLOGICAL MONITORING APPARATUS AND COMPUTER PROGRAM PRODUCT FOR A PHYSIOLOGICAL MONITORING APPARATUS

(75) Inventor: Börje Rantala, Helsinki (FI)

(73) Assignee: General Electric Company, Schenectady, NY (US)

( * ) Notice: Subject to any disclaimer, the term of this patent is extended or adjusted under 35 U.S.C. 154(b) by 521 days.

(21) Appl. No.: 12/787,941

(22) Filed: May 26, 2010

(65) Prior Publication Data

US 2011/0291837 A1    Dec. 1, 2011

(51) Int. Cl.
*G08B 1/08*    (2006.01)

(52) U.S. Cl.
USPC ............... 340/539.12; 340/539.11; 340/573.1

(58) Field of Classification Search
None
See application file for complete search history.

(56) References Cited

U.S. PATENT DOCUMENTS

| | | |
|---|---|---|
| 4,584,880 A | 4/1986 | Matzuk |
| 4,676,105 A | 6/1987 | Matzuk |
| 5,261,280 A | 11/1993 | Matzuk |
| 5,394,750 A | 3/1995 | Matzuk |
| 5,846,190 A | 12/1998 | Woehrle |
| 5,865,736 A | 2/1999 | Baker, Jr. et al. |
| 6,574,716 B2 | 6/2003 | Dovi |
| 6,602,201 B1 | 8/2003 | Hepp et al. |
| 6,684,090 B2 | 1/2004 | Ali et al. |
| 6,742,399 B2 | 6/2004 | Kunz et al. |
| 7,251,524 B1 | 7/2007 | Hepp et al. |
| 7,628,339 B2 | 12/2009 | Ivri et al. |
| 2002/0007685 A1 | 1/2002 | Kunz et al. |
| 2003/0214409 A1* | 11/2003 | Hickle ...................... 340/573.1 |
| 2007/0167753 A1 | 7/2007 | Van Wyk et al. |
| 2007/0249954 A1 | 10/2007 | Virag et al. |
| 2007/0249955 A1 | 10/2007 | Carlson et al. |
| 2007/0249956 A1 | 10/2007 | Carlson et al. |
| 2007/0265544 A1 | 11/2007 | Carlson et al. |
| 2008/0046024 A1 | 2/2008 | Carlson et al. |
| 2008/0228052 A1 | 9/2008 | Al-Ali |
| 2008/0269835 A1 | 10/2008 | Carlson et al. |
| 2008/0287756 A1 | 11/2008 | Lynn |
| 2008/0306397 A1 | 12/2008 | Bonmassar et al. |
| 2010/0016691 A1 | 1/2010 | Watson |

FOREIGN PATENT DOCUMENTS

WO    2008/081449 A2    7/2008

OTHER PUBLICATIONS

Makivirta et al., "The median filter as a preprocessor for a patient monitor limit alarm system in intensive care", Computer Methods and Programs in Biomedicine, Elsevier, Amsterdam, NL, vol. 24, No. 2-3, Feb. 1, 1991, pp. 139-144.*
Makivirta A et al., "The median filter as a preprocessor for a patient monitor limit alarm system in intensive care", Computer Methods and Programs in Biomedicine, Elsevier, Amsterdam, NL, vol. 24, No. 2-3, Feb. 1, 1991, pp. 139-144, XP024236955.
Search Report from corresponding EP Application No. EP11166748 dated Aug. 23, 2011.

* cited by examiner

*Primary Examiner* — Travis Hunnings
(74) *Attorney, Agent, or Firm* — Andrus, Sceales, Starke & Sawall, LLP

(57) ABSTRACT

A method for managing alarms in a physiological monitoring apparatus, a physiological monitoring apparatus, and a computer program product for a physiological monitoring apparatus are disclosed. A plurality of averages of a physiological parameter are derived, wherein the parameter is derived from at least one physiological signal acquired from a subject and wherein the averages represent a corresponding plurality of averaging periods. Respective alarm limits are assigned to the plurality of averages and at least one alarm indicator is defined, each alarm indicator being defined based on respective average and alarm limit. An alarm is detected based on the at least one alarm indicator.

23 Claims, 2 Drawing Sheets

ALARM GENERATION METHOD FOR PATIENT MONITORING, PHYSIOLOGICAL MONITORING APPARATUS AND COMPUTER PROGRAM PRODUCT FOR A PHYSIOLOGICAL MONITORING APPARATUS

BACKGROUND OF THE INVENTION

This disclosure relates generally to patient monitoring. More particularly, the present invention relates to generation of alarms in physiological monitoring apparatuses, termed patient monitors below.

Patient monitors are electronic devices designed to display physiological information about a subject. Electrocardiogram (ECG), electroencephalogram (EEG), plethysmographic signals, and signals related to blood pressure, temperature, and respiration represent typical physiological information contained in full-size patient monitors. Patient monitors are typically also furnished with alarming functionality to alert the nursing staff when a vital sign or physiological parameter of a patient exceeds or drops below a preset limit. Alarms are normally both audible and visual effects aiming to alert the staff to a life-threatening condition or to another event considered vital.

In addition to individual sensor/parameter alarms, patient monitors may be configured to raise combinatory alarms. That is, several physiological parameters may be used to determine a combined index and to give an alarm when the combined index fulfills a specific criterion. The combinatory alarms may range from simple combinations like "low heart rate and low arterial pressure" to complex rule-based scenarios used in various clinical support systems, for example. Below, the term physiological parameter is used to refer to the physiological variable to be monitored. As discussed above, the variable may be an individual parameter, such as heart rate or blood pressure, or a combinatory variable/index derived from multiple individual parameters. An individual physiological parameter may also represent a waveform signal value determined over a predefined period of time.

In most monitors, the alarm limits of a physiological parameter may be defined by the user, since the limits typically depend on patient etiology, age, gender, medication, and various other subjective factors. Each physiological parameter may also be assigned more than one alarm limit/criterion. That is, for a specific physiological parameter a patient monitor may raise alarms of different levels.

Alarm generation is a demanding task, as the patient monitor should be both sensitive and specific in producing alarms. In other words, the monitor should be able to recognize all true alarm events, without raising false or clinically irrelevant alarms. The difficulty of this task reflects in a real clinical environment where a large fraction of the alarms, even most alarms, may be considered to be false or at least clinically irrelevant. Such a large number of false or irrelevant alarms causes an enormous burden on the nursing staff and may also lead to impairment of the responses to true alarms.

It has been suggested to wait a given time period after the parameter crosses an alarm limit, thereby to reduce alarms caused by very short-time crossings that are likely to be caused by noise or signal artifacts. It has also been suggested to reduce nuisance alarms in a pulse oximeter by determining both the amount of time the measured value is past the limit and the amount by the limit is passed, and to inhibit an alarm based upon a combination of the said two amounts. The combination may be an integral that represents the area formed between the parameter envelope and the alarm limit after the crossing of the limit.

A drawback related to the alarm generation methods that start to analyze the signal and the nature of the alarm limit crossing in response to the detected crossing is the potential latency related to alarm initiation and also to alarm termination, especially if the parameter fluctuates near the alarm limit for a longer time and then a more sudden change occurs for the worse. This may be the case, for example, for a so-called decompensating patient whose body functions first try to compensate for the worsening physiological state. Consequently, the information obtained from the parameter is too positive during the compensation and the subsequent alarm may be delayed and assigned a low priority.

BRIEF DESCRIPTION OF THE INVENTION

The above-mentioned problems are addressed herein which will be comprehended from the following specification. In order to decrease the number of clinically irrelevant alarms, a plurality of averages of different averaging periods are determined, each average being assigned a respective alarm limit, and an alarm decision is made through analysis of the averages in view of the respective limits. The averages may be sliding averages determined substantially continuously. The mechanism prevents brief alarm level violations from causing clinically irrelevant alai ins and allows fast alarm generation/termination in various situations.

In an embodiment, a method for managing alarms in a physiological monitoring apparatus comprises determining a plurality of averages of a physiological parameter derived from at least one physiological signal acquired from a subject, wherein the averages represent a corresponding plurality of averaging periods. The method further comprises assigning respective alarm limits to the plurality of averages, defining at least one alarm indicator, wherein each alarm indicator is defined based on respective average and alarm limit, and detecting an alarm based on the at least one alarm indicator.

In another embodiment, a physiological monitoring apparatus for monitoring a subject comprises an averaging unit configured to determine a plurality of averages of a physiological parameter derived from at least one physiological signal acquired from a subject, wherein the averages represent a corresponding plurality of averaging periods and each average is assigned a respective alarm limit. The apparatus further comprises an analysis unit configured to define at least one alarm indicator, wherein each alarm indicator is defined based on respective average and alarm limit, and a detection unit configured to detect an alarm based on the at least one alarm indicator.

In a still further embodiment, a computer program product for a physiological monitoring apparatus comprises a first program product portion configured to determine a plurality of averages of a physiological parameter of a subject, wherein the averages represent a corresponding plurality of averaging periods and each average is assigned a respective alarm limit. The computer program product further comprises a second program product portion configured to define at least one alarm indicator, each alarm indicator being defined based on respective average and alarm limit and a third program product portion configured to detect an alarm based on the at least one alarm indicator.

Various other features, objects, and advantages of the invention will be made apparent to those skilled in the art from the following detailed description and accompanying drawings.

DETAILED DESCRIPTION OF THE INVENTION

Figure 1:
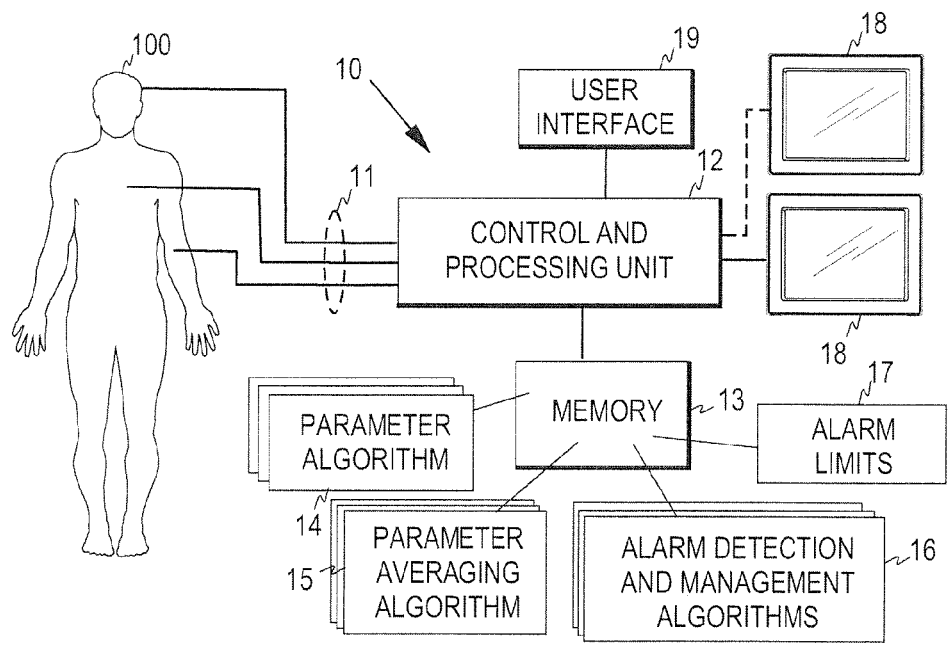
FIG. 1 illustrates one embodiment of an apparatus for monitoring patients.

FIG. 1 illustrates one embodiment of a physiological monitoring apparatus/system 10 for monitoring a subject/patient 100. A monitoring apparatus/system normally acquires a plurality of physiological signals 11 from the subject, where one physiological signal corresponds to one measurement channel. The physiological signals typically comprise several types of signals, such as ECG, EEG, blood pressure, respiration, and plethysmographic signals. Based on the raw real-time physiological signal data obtained from the subject, a plurality of physiological parameters may be determined, each physiological parameter being calculated from the waveform data of one or more of the physiological signals acquired from the subject. If a physiological parameter is derived from more than one physiological signal, i.e. from more than one measurement channel, the said physiological signals are usually of the same signal type. The physiological parameter may thus also represent a waveform signal value determined over a predefined period of time, although the physiological parameter is typically a distinct parameter derived from one or more physiological signals, such as heart rate derived from an ECG signal or an $SPO_2$ value derived from a plethysmographic signal.

The physiological signals 11 acquired from the subject are supplied to a control and processing unit 12 through a pre-processing stage (not shown) comprising typically an input amplifier and a filter, for example. The control and processing unit converts the signals into digitized format for each measurement channel. The digitized signal data may then be stored in the memory 13 of the control and processing unit. The digitized signal data is utilized by parameter algorithms 14 adapted to record, when executed by the control and processing unit, the time series of the physiological parameters to be monitored. The obtained time series of the physiological parameters may be stored in the memory. Below, alarm generation is discussed with respect to one physiological parameter, which may be heart rate, for example.

The control and processing unit uses a parameter averaging algorithm 15 to calculate a plurality of averages of the monitored parameter, such as heart rate. A dedicated averaging period, i.e. time constant, is used for each average, thereby to obtain average values defined over time periods of different lengths. In this context, averaging may involve various methods of applying a plurality of time constants to the data. In addition to arithmetic averaging, root-mean-square averaging, exponential averaging (infinite impulse response digital filters) or median filtering may be used, for example. The memory further stores a plurality of alarm limits 17, each limit forming an alarm limit for a particular average. The control and processing unit further uses alarm detection and management algorithms 16 to detect alarm events, to produce alarm notifications, and to manage the alarms. The algorithms 16 analyze the different averages in view of the respective alarm limits, and decide, based on the analysis, when an alarm is detected. The algorithms may further decide whether or not an alarm notification is to be produced in response to a detected alarm. The algorithms further handle an alarm detected, i.e. escalate and/or terminate the alarm. The handling may depend on the behavior of the averages and on user actions, for example. As discussed below, in logical sense the alarm generation and management algorithms may be divided into several functional entities.

The control and processing unit is further configured to control the display unit 18 of the apparatus. A display control algorithm may be stored in the memory of the control and processing unit and the apparatus may be provided with more than one display unit. The user may supply information and control the apparatus/system through user interface 19. In addition to the visual and/or audible effects possibly produced at a detected alarm event, an alarm may also be transmitted to an external monitoring unit through a network, for example.

Figure 2:
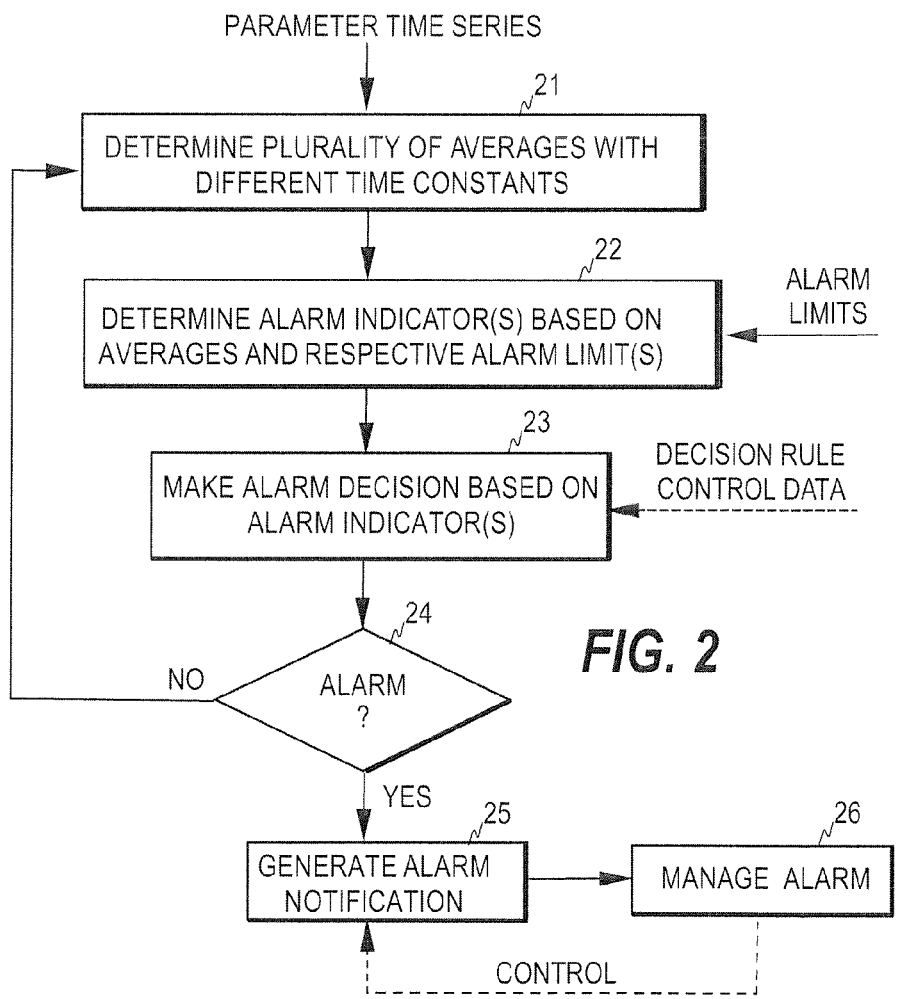
FIG. 2 is a flow diagram illustrating an embodiment of the generation of alarms in the apparatus of FIG. 1.

FIG. 2 is a flow diagram illustrating one embodiment of the operation of the control and processing unit for detecting and managing an individual alarm. A plurality of parameter averages are first determined in step 21 based on the parameter time sequence. Each average is determined using a dedicated averaging period, i.e. time constant. It is assumed here that six averages are calculated over 2, 4, 8, 16, 32, and 64 seconds, respectively. The control and processing unit then determines at least one alarm indicator based on the averages and the associated alarm limits 17 (step 22). Typically, an alarm indicator is a truth value determined based on respective average/limit pair, the truth value indicating whether or not the respective parameter average has reached/crossed the associated alarm limit, i.e. each truth value indicates whether an alarm is true or false in case of the corresponding average/limit pair. However, the alarm indicators may also be non-logical variables, such as variables that indicate the distance of each average from the respective alarm limit.

Consequently, six alarm indicators are typically obtained in this example. Based on the alarm indicator(s), a decision is then made whether or not an alarm event is present (step 23). The decision is made based on a predetermined alarm decision rule, which may be a fixed rule, or controllable through control data of various type. As is discussed below, the control data may include, for example, the averages determined in step 21.

If the alarm decision made in step 23 is negative (no alarm detection), the process continues the above process, i.e. returns to step 21 to repeat the above steps. New average values may be determined in a sliding manner, for example once in a second. If the alarm decision made in step 23 is affirmative (alarm detected), an alarm notification may be generated in step 25 to alert the nursing staff before the process starts to manage the alarm (step 26). The management may depend on various factors, such as user actions. It is to be noted here that even though the nursing staff is normally notified, in step 25, of an alarm detected in step 23, the generation of an alarm notification (audible and/or visual effects) is not necessary, but the alarm may be a hidden alarm. The generation of an alarm notification and the management of the alarm may depend on the alarm indicators. The averages or the alarm indicators may also be utilized to decide when to terminate the alarm and to return to "no alarm" state. The management process may control the alarm detection/generation process (steps 22, 23, and/or 25), so as to block detection/generation of a new alarm until the apparatus has returned to "no alarm" state with respect to the monitored parameter. This is illustrated with a dashed arrow in FIG. 2.

Figure 3:
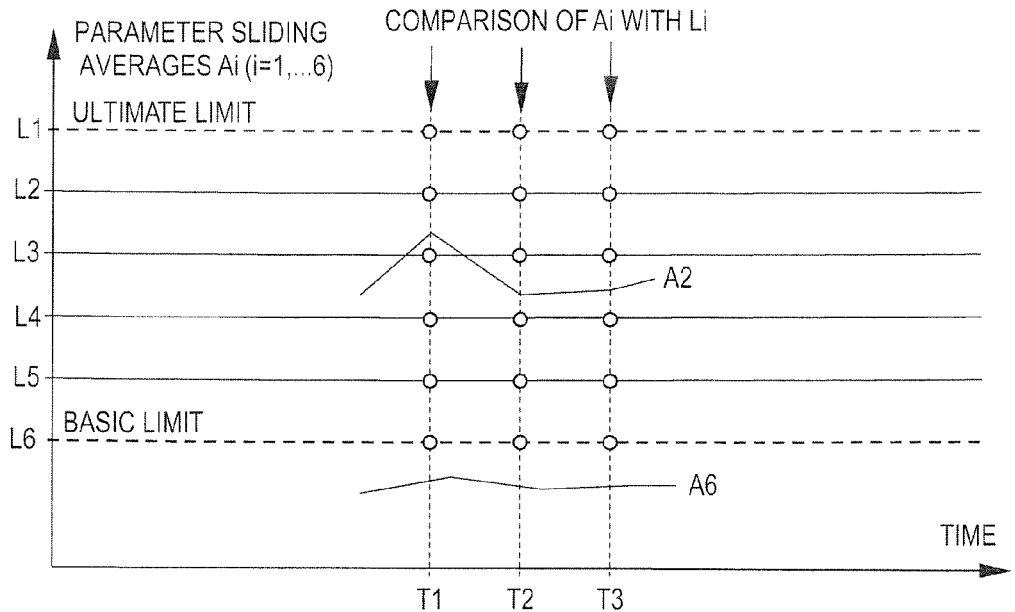
FIG. 3 illustrates an embodiment of the determination of alarm indicators.

FIG. 3 illustrates an example of steps 22 and 23 by showing a coordinate plane where the x coordinate represents time and the y coordinate the averages and the respective alarm limits. Using the above example, six averages Ai (i=1, 6) may be determined with time constants of $2^i$ seconds (2, 4, 8, 16, 32, and 64), respectively. Each average Ai is assigned an alarm limit Li so that the slowest average A6 (64 second average) is associated with a basic alarm limit L6. It is assumed here that the severity/criticality increases as the parameter values increase, which is the case for heart rate, for example. The figure shows three successive decision-making instants T1-T3. At each time instant, average Ai is compared with respective alarm limit Li, as is illustrated with small circles, thereby to obtain an alarm indicator value, typically a logical truth value.

In order that the user does not have to adjust several alarm limits, the control and processing unit may determine the ultimate alarm limit L1 (that corresponds to the fastest average) based on the basic alarm limit L6, which may be determined by the user. The determination of L1 may be carried out, for example, as follows: L1=P×L6+F, where P is a predetermined coefficient (such as 1.10) and F a predetermined constant (such as 10). Consequently, the only limit that needs to be controlled by the user is the basic alarm limit L6. The intermediate alarm limits L2-L5 may be obtained, for example, by dividing the limits evenly between the basic alarm limit and the ultimate alarm limit, as is shown in FIG. 3.

Figure 4:
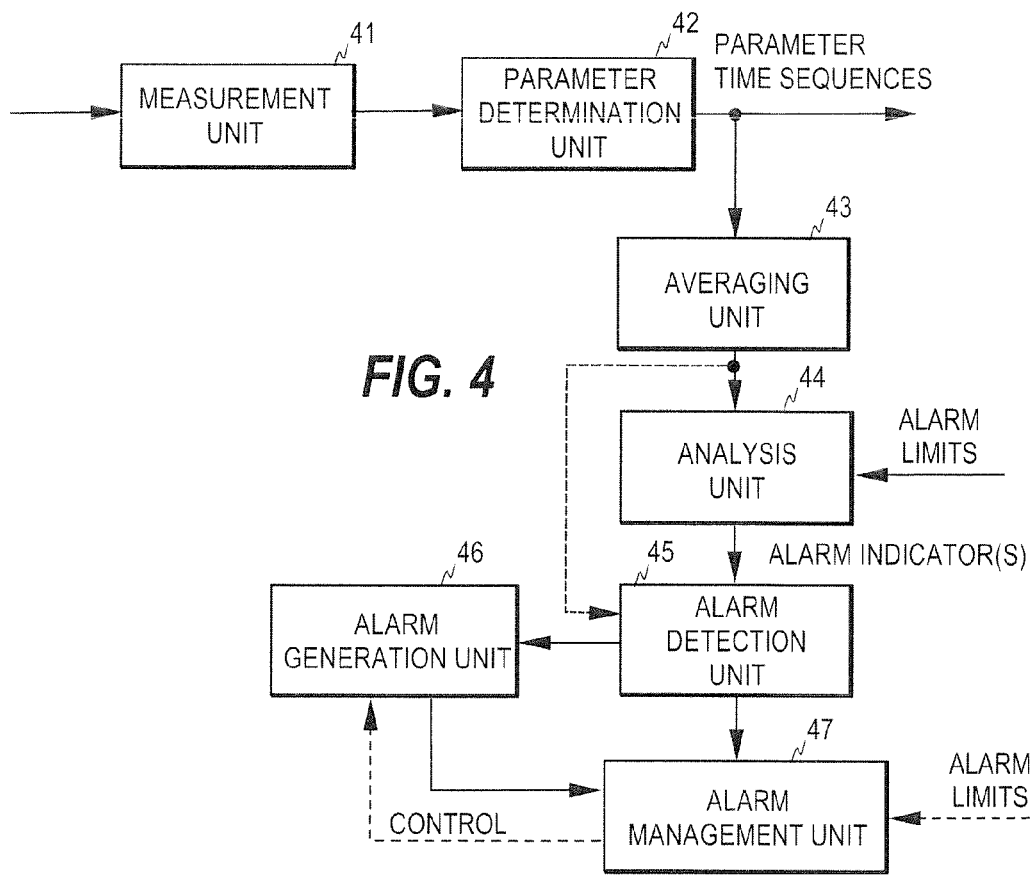
FIG. 4 illustrates an example of the functional entities of a patient monitor in terms of alarm generation.

In terms of the alarm detection and management, the functionalities of the control and processing unit 12 may be divided, in logical sense, into several functional entities shown in FIG. 4. A measurement unit 41 is configured to measure the physiological signal data from the subject. A parameter determination unit 42 is configured to determine, based on at least one physiological signal, the physiological parameter(s) to be monitored. An averaging unit 43 is configured to derive, from each parameter to be monitored, a plurality of concurrent averages of different averaging periods. The averaging unit thus outputs averages Ai that change at different rates due to the different time constants. An analysis unit 44 is configured to analyze at least one of the current values of the averages, thereby to obtain at least one alarm indicator value. Typically, the analysis unit produces a plurality of truth values by comparing the current value of each average with the respective alarm limit. The result of each comparison indicates whether or not the average has reached/crossed the respective alarm limit. The analysis unit may also produce non-logical variables, such as variables that indicate the distance of an average from the respective alarm limit. It assumed here that the analysis unit is further configured to define the alarm limits based on user input and to associate the alarm limits with the respective averages.

An alarm detection unit 45 is configured to make the final alarm decision based on the alarm indicator(s). The alarm detection unit may use different predefined rules for making the final alarm decision. The operation of the alarm detection unit depends, for example, on whether the analysis unit outputs logical or non-logical values. In one embodiment relating to the use of logical values, an affirmative alarm decision is made if the truth values indicate that at least n (n≧2) averages have reached/crossed the respective alarm limit values. The value of n may be selected in view of a majority decision, for example. However, the final decision on the occurrence of an alarm event may also be made using simple OR logic. That is, an alarm may be detected in unit 45 if any of the averages has reached/crossed the respective limit value. The final alarm decision may also be made without determining all truth values, i.e. immediately when one or more of the truth values indicate that an affirmative decision can be made without analyzing the rest of the averages. Therefore, it is possible that the analysis unit does not have to analyze all averages. Different weights may also be used for the averages, so that a certain subset of the averages may determine the final result regardless of the other averages. If the analysis unit outputs non-logical values, the detection unit may determine a final alarm value based on the said values and compare the final alarm value to an alarm threshold, thereby to decide whether or not an alarm is detected.

In one embodiment, the averages, or other variables derived from the parameter, may be used to change the alarm decision rule. For example, if it is detected that one or more of the averages with long time-constants are near to the respective alarm limits, the rule may be changed so that an alarm is detected if any one or more of the averages with short time-constants indicate an alarm. For making the rule change decision, the control and processing unit may also examine the said average(s) of long time-constant(s) over a certain time window. In anticipation of the occurrence of certain critical events, the alarm detection unit may thus change the alarm decision rule based on the averages, thereby to increase the rapidity of the alarm detection. The apparatus may also calculate various variables from the averages or the parameter, which provide further information about the behaviour of the parameter, and change the alarm decision rule based on the variables. For example, certain detected topologies of the parameter waveform may be used to change the alarm decision rule.

The alarm detection unit controls an alarm generation unit 46 configured to generate alarms based on the decisions made in the alarm detection unit. The alarm detection unit or the alarm generation unit may also determine, based on the alarm indicators, an initial priority level for the alarm. For example, the initial priority level may be determined according to the number of alarm indicators indicative of an alarm: the greater the number, the higher the initial priority level of the alarm. Another alternative is to increase the priority according to the amount of the alarm limit crossing. A combination of the number and amount may also be used to determine the priority level. The change of the alarm decision rule may be also be accompanied by a change in the manner the priority level is determined, especially if the rule change is made in anticipation of a critical event.

An alarm management unit 47 is configured to manage each alarm generated. The management includes escalation and termination of alarms, for example. For this, the unit may utilize the averages determined in the averaging unit or the alarm indicators determined in the analysis unit. For example, the alarm management unit may control the escalation of a detected alarm according to the alarm indicators (where escalation refers to a process that extends the alarm from a lower to a higher level of priority/severity, if the alarm persists and/or goes unacknowledged long enough). This may be carried out regardless of whether or not an initial priority level is determined for the alarm. That is, the alarm may be escalated from any level of priority, except the highest. Further, the alarm management unit may decide to terminate an existing alarm when k (k=1, 2, . . . ) fastest averages start(s) to indicate "no alarm". The alarm management unit may control any one or more of units 44-46, so as to block detection or generation of a new alarm until the apparatus has returned to "no alarm" state with respect to the parameter in question.

It is to be noted that FIG. 4 illustrates the division of the functionalities of the control and processing unit in logical sense and in view of the alarm generation. In a real apparatus the functionalities may be distributed in different ways between the elements or units of the apparatus. That is, the apparatus may comprise the above functional units only at logical level. Moreover, the apparatus may be implemented as an auxiliary monitor utilizing the physiological data collected by another device. Units 41 and 42 may therefore belong to another device to which the auxiliary monitor is connectable.

A conventional patient monitor may be upgraded to enable the monitor to control the alarm escalation in the above-described manner. Such an apparatus upgrade may be implemented, for example, by delivering to the monitor a software module that may contain the above functionalities. The software module may be delivered, for example, on a data carrier, such as a CD or a memory card, or through a telecommunications network. However, since the software module may utilize the parameters already determined by the monitor, the software module may comprise, for example, software portions that correspond to functional entities 43-45 of FIG. 4.

The above-described combination of averages of different averaging periods allows rapid detection of an alarm event regardless of the behavior of the parameter. For example, the use of the combination prevents brief alarm level violations from causing clinically irrelevant alarms, because brief violations do not have a significant effect on averages having a longer time-constant. However, the averages of longer time-constants give an indication if the parameter fluctuates around the alarm limit. The above-described mechanisms also allow fast alarm generation/termination in case of various parameter changes, since the averages with shorter time-constants give a quick indication of the current trend of the parameter. Thus, if the patient has been near the alarm limit for a longer period and then an alarm crossing is detected, an alarm may be raised rapidly. Furthermore, as the averages are determined continuously, the information necessary for the alarm decision is also available continuously.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural or operational elements that do not differ from the literal language of the claims, or if they have structural or operational elements with insubstantial differences from the literal language of the claims.

The invention claimed is:

1. A method for managing alarms in a physiological monitoring apparatus, the method comprising:
   determining a plurality of averages of a physiological parameter derived from at least one physiological signal acquired from a subject, wherein the averages represent a corresponding plurality of averaging periods;
   assigning respective alarm limits to the plurality of averages;
   defining at least one alarm indicator, wherein each alarm indicator is defined based on at least one of the respective averages and corresponding alarm limits; and
   detecting an alarm based on the at least one alarm indicator:
   wherein the assigning includes assigning a basic alarm limit to a first average of the plurality of averages, wherein the first average represents the longest averaging period of the plurality of averages; and
   wherein the assigning further includes determining an ultimate alarm limit based on the basic alarm limit and assigning the ultimate alarm limit to a second average of the plurality of averages, wherein the second average represents the shortest averaging period of the plurality of averages.

2. The method according to claim 1, wherein the assigning includes assigning dedicated alarm limits for averages between the first average and the second average, wherein the order of the dedicated alarm limits corresponds to length order of the averaging periods.

3. The method according to claim 2, wherein the assigning includes assigning the dedicated alarm limits, in which the dedicated alarm limits are evenly spaced between the basic alarm limit and the ultimate alarm limit.

4. The method according to claim 1, wherein the defining includes defining a plurality of alarm indicators, in which each alarm indicator is an alarm truth value defined based on respective average/alarm limit pair.

5. The method according to claim 4, wherein the detecting includes one of
   forming a logic combination of the alarm truth, values; and
   detecting the alarm if at least a predetermined number of the alarm indicators indicate an alarm.

6. The method according to claim 1, further comprising determining, based on the at least one alarm indicator, an initial priority level for the alarm.

7. The method according to claim 1, where the determining rule is $L1=P \times L6+F$, where P is a predetermined coefficient and F a predetermined constant.

8. The method according to claim 7 where P and F are predetermined by the clinical user.

9. A physiological monitoring apparatus for monitoring a subject, the apparatus comprising:
   an averaging unit configured to determine a plurality of averages of a physiological parameter derived from at least one physiological signal acquired from a subject, wherein the averages represent a corresponding plurality of averaging periods and each average is assigned a respective alarm limit;
   an analysis unit configured to define at least one alarm indicator, wherein each alarm indicator is defined based on at least one of the respective averages and corresponding alarm limits; and
   a detection unit configured to detect an alarm based on the at least one alarm indicator
   wherein a basic alarm limit is assigned to a first average of the plurality of averages, and wherein the first average represents the longest averaging period of the plurality of averages; and
   wherein the apparatus is further configured to determine an ultimate alarm limit based on the basic alarm limit and to assign the ultimate alarm limit to a second average of the plurality of averages wherein the second average represents the shortest averaging period of the plurality of averages.

10. The apparatus according to claim 9, wherein dedicated alarm limits are assigned to averages between the first average and the second average, in which the order of the dedicated alarm limits corresponds to length order of the averaging periods.

11. The apparatus according to claim 10, wherein the dedicated alarm limits are evenly spaced between the basic alarm limit and the ultimate alarm limit.

12. The apparatus according to claim 9, wherein the analysis unit is configured to define a plurality of alarm indicators, in which each alarm indicator is an alarm truth value defined based on respective average/alarm limit pair.

13. The apparatus according to claim 12, wherein the detection unit is configured to perform one of the following
   form a logic combination of the truth values and
   detect an alarm if at least a predetermined number of the alarm indicators indicate an alarm.

14. The apparatus according to claim 9, wherein the ultimate alarm limit corresponds to a value obtained by multiplying the basic limit by a predetermined coefficient and adding a predefined fixed constant.

15. The apparatus according to claim 9, wherein the detection unit is further configured to determine, based on the at least one alarm indicator, an initial priority level for the alarm.

16. A computer program product for a physiological monitoring apparatus, the computer program product comprising:
a first program product portion configured to determine a plurality of averages of a, physiological parameter of a subject, wherein the averages represent a corresponding plurality of averaging periods and each average is assigned a respective alarm limit;
a second program product portion configured to define at least one alarm indicator, each alarm indicator being defined based on at least one of the respective averages and corresponding alarm limits; and
a third program product portion configured to detect an alarm based on the at least one alarm indicator
wherein the first program product portion assigns a basic alarm limit to a first average of the plurality of averages, wherein the first average represents the longest averaging period of the plurality of averages; and
wherein the first program product portion further determines an ultimate alarm limit based on the basic alarm limit and assigns the ultimate alarm hunt to a second average of the plurality of averages, wherein the second average represents the shortest averaging period of the plurality of averages.

17. A method for managing alarms in a physiological monitoring apparatus, the method comprising:
determining a plurality of averages of a physiological parameter derived from at least one physiological signal acquired from a subject wherein the averages represent a corresponding plurality of averaging periods;
assigning respective alarm limits to the plurality of averages;
defining at least one alarm indicator, wherein each alarm indicator is defined based on at least one of the respective averages and corresponding alarm limits;
detecting an alarm based on the at least one alarm indicator; and
determining, based on the at least one alarm indicator, an initial priority level for the alarm, wherein the detecting includes employing an alarm decision rule, in which the detecting further includes changing the alarm decision rule based on the plurality of averages.

18. The method according to claim 17 comprising the additional step of de-escalating an existing alarm when the alarm indicator associated with the shortest averaging period indicates no alarm.

19. A physiological monitoring apparatus for monitoring a subject, the apparatus comprising:
an averaging unit configured to determine a plurality of averages of a physiological parameter derived from at least one physiological signal acquired from a subject, wherein the averages represent a corresponding plurality of averaging periods and each average is assigned a respective alarm limit;
an analysis unit configured to define at least one alarm indicator, wherein each alarm indicator is defined based on at least one of the respective averages and corresponding alarm limits: and
a detection unit configured to detect an alarm based on the at least one alarm indicator,
wherein the detection unit is configured to employ an alarm decision rule, in which the detection unit is further configured to change the alarm decision rule based on the plurality of averages.

20. A method for managing alarms in a physiological monitoring apparatus, the method comprising:
determining a plurality of averages of a physiological parameter derived from at least one physiological signal acquired from a subject, wherein the averages represent a corresponding plurality of averaging periods;
assigning respective alarm limits to the plurality of averages;
defining at least one alarm indicators, wherein each alarm indicator is defined based on at least one of the respective averages and corresponding alarm limits;
detecting an alarm based on the at least one alarm indicator; and
de-escalating an existing alarm when the alarm indicator associated with a shortest averaging period of the plurality of averages indicates no alarm.

21. The method according to claim 20 where the alarm de-escalation includes terminating the alarm.

22. The method according to claim 20 where the alarm de-escalation does not terminate the alarm, but reduces the priority.

23. The method according to claim 22 where the alarm de-escalation does not terminate the alarm, and keeps silencing continuity.

* * * * *